United States Patent
Ueno et al.

(10) Patent No.: US 9,990,450 B2
(45) Date of Patent: Jun. 5, 2018

(54) SIMULATION METHOD FOR HIGH POLYMER MATERIAL

(75) Inventors: Shinichi Ueno, Kobe (JP); Yasumasa Bito, Kobe (JP); Hiroyuki Kishimoto, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 992 days.

(21) Appl. No.: 14/360,432

(22) PCT Filed: Jul. 25, 2012

(86) PCT No.: PCT/JP2012/068764
§ 371 (c)(1),
(2), (4) Date: Jun. 12, 2014

(87) PCT Pub. No.: WO2013/077027
PCT Pub. Date: May 30, 2013

(65) Prior Publication Data
US 2014/0297239 A1 Oct. 2, 2014

(30) Foreign Application Priority Data
Nov. 24, 2011 (JP) ................................. 2011-256493

(51) Int. Cl.
*G06F 7/60* (2006.01)
*G06F 17/10* (2006.01)
(Continued)

(52) U.S. Cl.
CPC ........ *G06F 17/5009* (2013.01); *G06F 19/704* (2013.01); *G06F 19/701* (2013.01)

(58) Field of Classification Search
None
See application file for complete search history.

(56) References Cited

U.S. PATENT DOCUMENTS

2011/0288838 A1* 11/2011 Hamatani ................ G01N 3/00
703/6

FOREIGN PATENT DOCUMENTS

JP  2003-012566 A  1/2003
JP  2006-064658 A  3/2006
(Continued)

OTHER PUBLICATIONS

Kairn, T. et al., "Molecular-Dynamics Simulation of Model Polymer Nanocomposite Rheology and Comparison with Experiment", Nov. 14, 2005, The Journal of Chemical Physics 123, Americal Institute of Physics.*
(Continued)

*Primary Examiner* — Cedric Johnson
(74) *Attorney, Agent, or Firm* — Birch, Stewart, Kolasch & Birch, LLP

(57) ABSTRACT

A computerized simulation method for evaluating dispersion of fillers in a high polymer material includes a step of defining a filler model comprising at least one particle, a step of defining a polymer model comprising a plurality of particles each having a first potential with respect to the particle of the filler model, a step of performing a molecular dynamics calculation of the filler model and the polymer model placed in a predetermined virtual space on the computer, and a step of observing the dispersion of the filler model from data obtained in the molecular dynamics calculation. The polymer model further includes at least one modified basal particle having a second potential with respect to the particle of the filler model, and the second potential differs from the first potential.

7 Claims, 5 Drawing Sheets

(51) Int. Cl.
  G06F 17/50    (2006.01)
  G06F 19/00    (2018.01)

(56) References Cited

FOREIGN PATENT DOCUMENTS

| JP | 2007-233859 A | | 9/2007 |
|---|---|---|---|
| JP | 2008-065556 A | | 3/2008 |
| JP | 2009-110228 A | | 5/2009 |
| JP | 2012177609 A | * | 9/2012 |

OTHER PUBLICATIONS

Brown, D. et al., "A Molecular Dynamics Study of a Model Nanoparticle Embedded in a Polymer Matrix", Jan. 18, 2003, Macromolecules 36, American Chemical Society.*

Yagyu, Hiromasa et al., "Coarse-Grained Molecular Dynamics Simulation of Nanofilled Crosslinked Rubber", 2009, Computational Materials Science 46, Elsevier B.V.*

Jouault, Nicolas et al., "Well-Dispersed Fractal Aggregates as Filler in Polymer-Silica Nanocomposites: Long-Range Effects in Rheology", Feb. 18, 2009, Macromolecules, 42, American Chemical Society.*

Raos et al., "Computational Experiments on Filled Rubber Viscoelasticity: What Is the Role of Particle-Particle Interactions?", pp. 6744-6751, Macromolecules vol. 39, 2006.

Brown et al., "Effect of Filler Particle Size on the Properties of Model Nanocomposites," Macromolecules, vol. 41, 2008 (published on web Jan. 25, 2008), pp. 1499-1511.

Extended European Search Report, dated Sep. 9, 2015, for European Application No. 12850926.2.

Liu et al., "Nanoparticle Dispersion and Aggregation in Polymer Nanocomposites: Insights from Molecular Dynamics Simulation," Langmuir, vol. 27, May 19, 2011, pp. 7926-7933.

* cited by examiner

SIMULATION METHOD FOR HIGH POLYMER MATERIAL

TECHNICAL FIELD

The present invention relates to a simulation method for a high polymer material useful for evaluating or improving filler dispersion.

BACKGROUND ART

These days, various type of computerized simulations (numerical calculation) for a high polymer material have been proposed. This kind of simulation is mainly based on a coarse-graining molecular dynamics (MD) calculation.

In the molecular dynamics calculation, a material model that includes a plurality of computational particles is firstly defined based on the molecular structure of a high polymer material to be analyzed, wherein each particle represents an atom, a group thereof, a molecule of the molecular structure and the like. Then, a computer calculates the position of each particle of the material model with a small time interval based on a motion equation of the Newton.

According to such a molecular dynamics calculation, it may be possible to trace a microscopic movement of each particle of the material model. Thus, the property and microscopic movement of the high polymer material is analyzed without experiment. Furthermore, better simulation result that does not depend on an initial configuration of particles of the material model may be obtained by providing enough trace time.

RELATED ART DOCUMENTS

Patent Documents

[Patent Document 1] Japanese Unexamined Patent Application Publication No. 2006-64658
[Patent Document 2] Japanese Unexamined Patent Application Publication No. 2007-233859
[Patent Document 3] Japanese Unexamined Patent Application Publication No. 2009-110228

SUMMARY OF INVENTION

Problem to be Solved by the Invention

A high polymer material such as rubber and the like contains fillers such as carbon black, or silica. It is well known in the art that the filler affects the property of the rubber.

Unfortunately, since the conventional simulation method is made using the material model that employs a uniform polymer model and a filler model, it may be difficult to evaluate filler dispersion in an actual high polymer material.

The present invention has been worked out in light of the circumstances described above, and has a main object of providing a simulation method for a high polymer material useful for evaluating or improving filler dispersion in an actual high polymer material by modifying a polymer model so as to include a modified basal particle having a different potential with respect to a non-modified particle.

Means for Solving the Problem

In accordance with the present invention, there is provided a computerized simulation method for evaluating dispersion of fillers in a high polymer material, the method comprising defining a filler model available for use with the computerized simulation, the filler model comprising at least one particle, defining a polymer model available for use with the computerized simulation, the polymer model comprising a plurality of particles each having a first potential with respect to the particle of the filler model, and at least one modified basal particle having a second potential with respect to the particle of the filler model, wherein the second potential differs from the first potential, performing a molecular dynamics calculation of the filler model and the polymer model placed in a predetermined virtual space on the computer, and observing the dispersion of the filler model from data obtained in the molecular dynamics calculation.

In another aspect of the invention, the filler model may comprise a plurality of particles.

In another aspect of the invention, the method may further comprise linking the particle of the filler model to the modified basal particle of the polymer model, when the modified basal particle of the polymer model approaches to the particle of the filler model within a predetermined distance in the molecular dynamics calculation.

In another aspect of the invention, each of the first potential and the second potential may be defined so as to occur a repulsive force between two particles, and the repulsive force based on the second potential is weaker than that of the first potential.

According to the present invention, the filler dispersion in a high polymer material may be evaluated.

An actual high polymer material is usually added a modifying agent to modify the structure or chemical properties of bases thereof. The present invention includes the polymer model including at least one modified basal particle having a potential different from that of a non-modified particle of the polymer model. Thus, according to the present invention may evaluate dispersion of fillers in an actual high polymer material that contains a modified agent through the molecular dynamics calculation. It may helpful to develop a new high polymer material by evaluating effect of a modified agent (a modified base).

DESCRIPTION OF THE NUMERALS 2 non-modified particle of polymer model
3 polymer model
5 modified basal particle of polymer model
6 particle of filler model
7 filler model

MODE FOR CARRYING OUT THE INVENTION

An embodiment of the present invention will be explained below with reference to the accompanying drawings. The embodiment of the present invention provides for a computerized simulation method for evaluating dispersion of fillers in a high polymer material. Here, the term "high polymer material" is intended to include at least rubber, resin and elastomer. The term "filler" is intended to include at least carbon black, silica and alumina.

Figure 1:
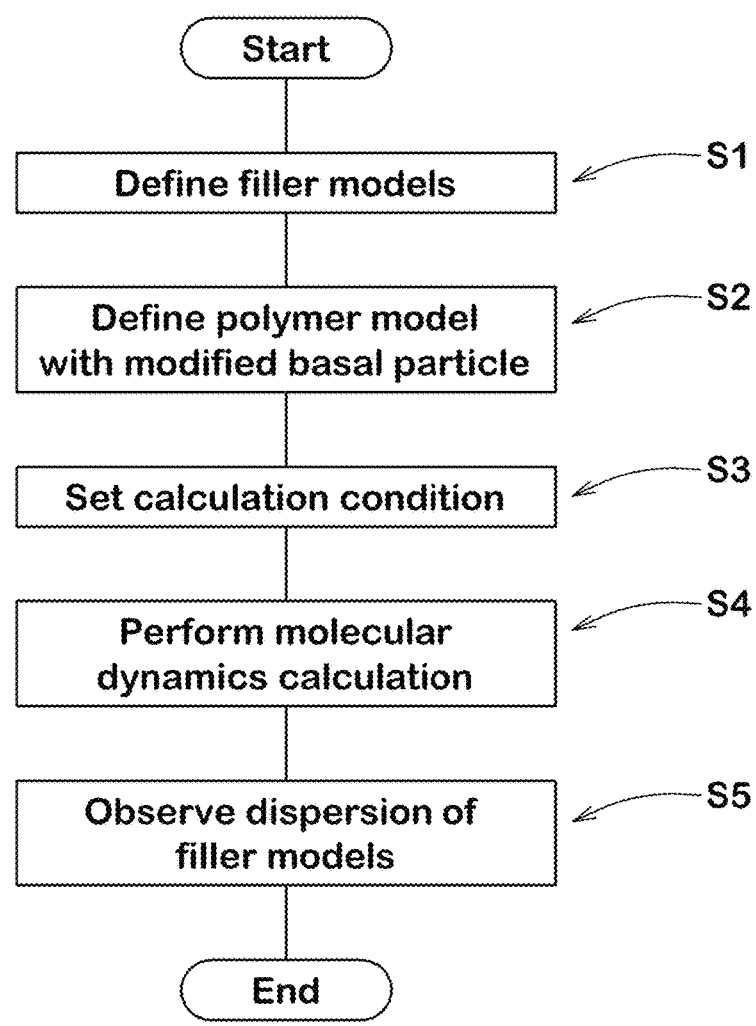
FIG. 1 is a flow chart of the simulation method in this embodiment.

FIG. 1 illustrates a flowchart of the simulation method as an embodiment of the present invention. The simulation method in accordance with the present embodiment includes defining a filler model available for use with the computerized simulation, wherein the filler model includes at least one particle (Step S1). The filler model corresponds to numerical data stored in a computer to represent behavior of the filler in the molecular dynamics calculation.

Figure 2:
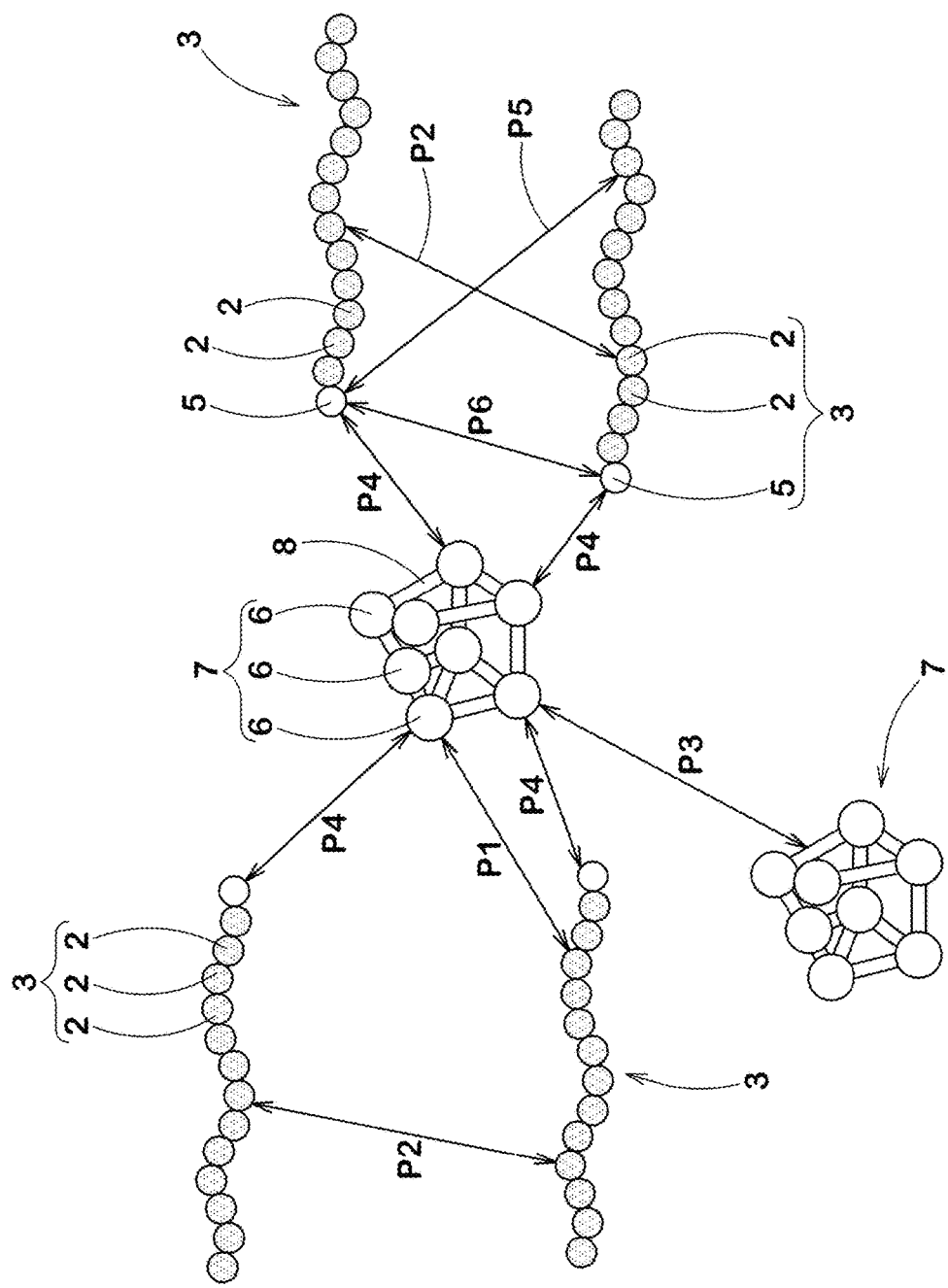
FIG. 2 is a diagram illustrating a filler model, and a polymer model with a modified basal particle.

FIG. 2 illustrates an embodiment of the visualized filler model 7. The filler model 7 has a three-dimensional configuration that includes a plurality of particles 6, and a bonding chain 8 connecting between two particles 6 and 6. In this embodiment, nine particles 6 are employed to define the filler model 7. The filler model 7 is defined to simulate behavior of the filler for reinforcing rubber material. In this embodiment, the three-dimensional configuration of the filler model 7 is determined based on actual silica. The bonding chain 8 functions to maintain a certain bond length between two particles 6 and 6 of the filler model 7. The bonding chain 8 is stored in the computer as a computational spring element having its equilibrium length and spring constant.

Next, the simulation method includes defining a polymer model 3 available for use with the computerized simulation (Step S2), wherein the polymer model 3 includes a plurality of particles, preferably at least three particles. In this embodiment, the polymer model 3 includes fourteen particles 2 and 5. In the molecular dynamics calculation, the polymer model 3 corresponds to numerical data stored in the computer to represent behavior of the polymer in the high polymer material.

FIG. 2 illustrates an embodiment of the visualized polymer model 3. The polymer model 3 in accordance with the present embodiment has a three-dimensional straight chain configuration that includes a plurality of particles (non-modified particles) 2, a modified basal particle 5, and bonding chains (not illustrated) each connecting between two particles.

Next, necessary conditions for the molecular dynamics calculation are set (step S3), and then the molecular dynamics calculation is performed using the filler model 7 and the polymer model 3 placed in a predetermined virtual space on the computer (Step S4).

Each of the particles 6 of the filler model 7 and the particles 2 and 5 of the polymer model 3 represents a material point in the motion equation used in the molecular dynamics calculation. Thus, the conditions include at least a mass, a volume, a diameter, and the initial position of each of the particles 2, 5 and 6. Furthermore, since the molecular dynamics calculation is performed in the virtual space (a cell) in which the filler model 7 and the polymer model 3 are arranged, a boundary condition for the cell may be set. In addition, potential is set among particles 2, 5 and 6. The conditions described above are stored in the computer as numeric data.

The potential is a function of the distance between two concerned particles to calculate a force that acts therebetween. In this example, for the following combinations of two particles, potentials P1-P6 are defined:
particles 2-6: potential P1,
particles 2-2: potential P2,
particles 6-6: potential P3,
particles 5-6: potential P4,
particles 2-5: potential P5, and
particles 5-5: potential P6.

In this example, the potential is given by the following expression (1):

$$U = 0.5 a_{ij}(1 - r_{ij}/r_c)^2 \quad (1)$$

Here, $a_{ij}$ is the strength of the potential defined between the particles concerned, $r_{ij}$ is the distance between the centers of the particles concerned, and $r_c$ is the cutoff distance predetermined between the centers of the particles concerned. With the expression (1), the potential is defined such that a repulsive force occurs if the distance $r_{ij}$ is decreased under the cutoff distance $r_c$. If the distance $r_{ij}$ is equal to the cutoff distance $r_c$, the potential U is zero and no repulsive force occurs between the particles. In this example, the cutoff distance $r_c$ is set at 1[σ].

The potential P1-P6 may be adjusted by changing the value of the strength $a_{ij}$ in the expression (1). In this example, the strength aij of the potentials are set as follows:
potential P1: $a_{ij}$=72,
potential P2: $a_{ij}$=50,
potential P3: $a_{ij}$=50,
potential P4: $a_{ij}$=12,
potential P5: $a_{ij}$=50, and
potential P6: $a_{ij}$=50.

In this embodiment, a coarse-graining molecular calculation, especially a technique called as "DBP (Dissipative Particle Dynamics)" is employed for the molecular calculation. The original paper of DBP technique (J. Chem Phys. 107 (11) 4423-4435 (1997)) proposed to use the potential having the parameter $a_{ij}$ of 25 between the same kinds of particles. As a result of many researches, the potential having the parameter $a_{ij}$ of 50 between the same kinds of particles, and the parameter $a_{ij}$ of 72 between the different kinds of particles came out (for example, Macromolcule vol. 39 6744 (2006)). In this embodiment, these parameters are employed. In addition, the parameter $a_{ij}$ of 12 is given as an example of a value lower than the $a_{ij}$ of 50.

Further, the parameters $a_{ij}$ (=12) of the potential P4 between the particles 6 of the filler model 7 and the modified basal particle 5 of the polymer model 3 is set weaker than the parameter $a_{ij}$ (=72) of the potential P1 between the particle 6 of the filler model 7 and the particle 2 of the polymer model 3. Accordingly, the repulsive force based on the potential between the modified basal particle 5 of the polymer model 3 and the particle 6 of the filler model 7 is weaker than the repulsive force between the particle 2 of the polymer model 3 and the particle 6 of the filler model 7 in the molecular calculation. In other words, the modified basal particle 5 is defined the potential so as to have high affinity to the particle 6 of the filler model 7, as compared to the particle 2.

In an actual case, a modifying agent for giving affinity may be blended into an high polymer material. In the computer simulation, the modified basal particle 5 (a modified polymer) of the polymer model 3 with a high affinity property may represent such a modifying agent or modified polymer each of which controls dispersion of fillers in the actual high polymer material. In this embodiment, each potential of the particles 2, 5 and 6 is defined by the formula (1). Thus, the modified basal particle may be introduced into the molecular dynamics calculation easily by adjusting the parameter $a_{ij}$.

Figure 3A:
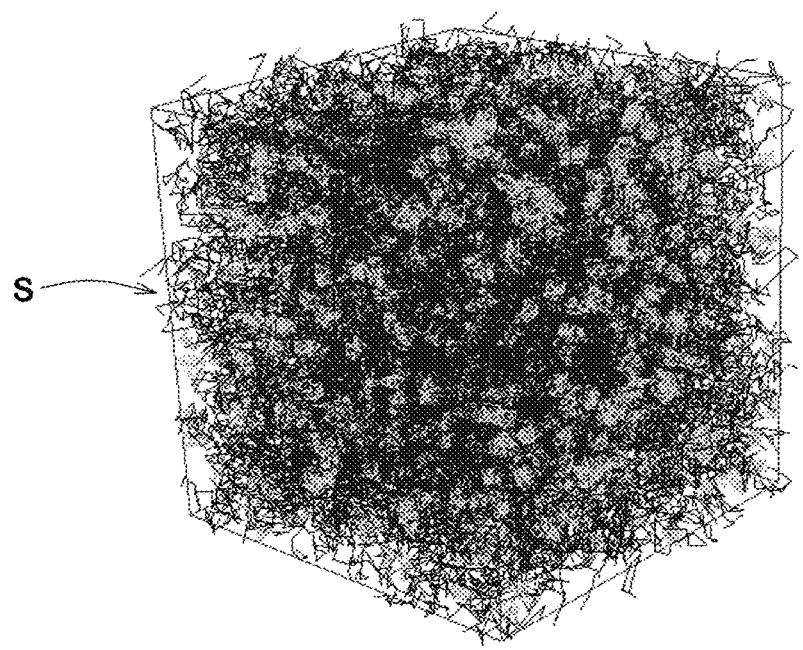
FIG. 3A is a perspective view of a simulation model in a state before performing a molecular dynamics calculation.

To perform the molecular dynamics calculation on the computer, as shown in FIG. 3(a), the polymer model 3 and the filler model 7 are initially placed in the cell S having a predetermined space. The cell S is a virtual space that corresponds a micro part of the high polymer material to be analyzed. The cell S in this embodiment is defined as a cube having each side of 24.7σ. Here, "σ" means a unit for length used in the coarse graining molecular dynamics calculation. In this embodiment, the polymer models 3 of 2,571 and the filler models 7 of 1,000 are initially placed in random in the cell S.

Assuming that all of the models 3 and 7 follow the classical dynamics, the calculation according to Newton's equation of motion is made about the cell S during a given time period in the molecular dynamics calculation, and the motion of each of the particles 2, 5 and 6 is tracked at each time step during the time period. During the molecular dynamics calculation, the conditions such as the numbers of the respective filler particles, the volume of the cell, and the temperature of the cell are maintained constant. The molecular dynamics calculation may be finished when a predetermined number of steps are completed (200,000 steps, for example).

Next, a step (Step S5) of observing for dispersion of filler models 7 is performed based on the results of the molecular dynamics calculation. Usually, fillers exhibit a good reinforcing effect by being dispersed uniformly in the polymer. Thus, it is important to include the step of observing the dispersion of the filler model 7.

Figure 3B:
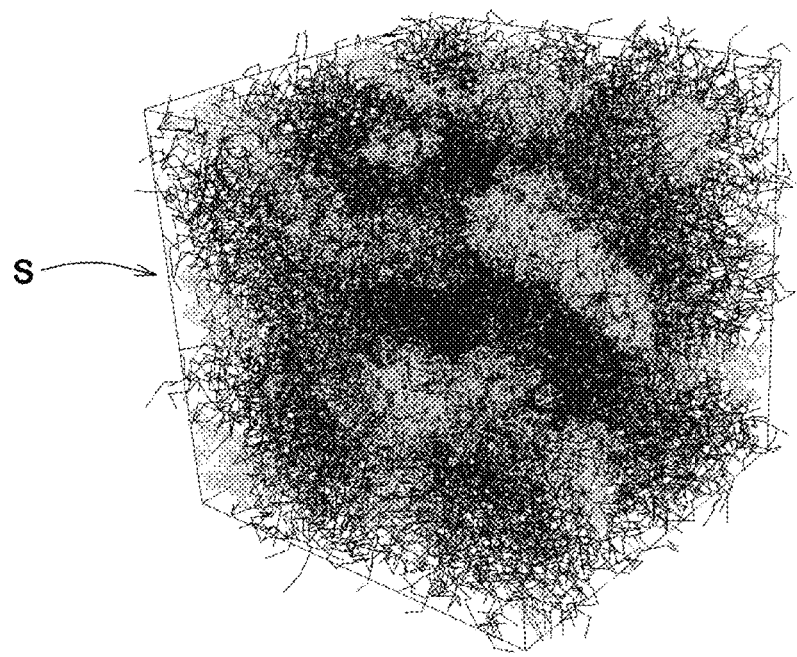
FIG. 3B is a perspective view of the simulation model in a state after performing the molecular dynamics calculation.

FIG. 3(b) illustrates a result of the molecular dynamics calculation. In FIG. 3(b), the filler models 7 displayed by the whitish color is dispersed in a relatively wide range. From the result of FIG. 3(b), it is assumed that dispersion of fillers may be changed (improved) by offering a modifying agent. The observing step may be observed by the naked eyes of an observer through a display device that shows a visualized calculation result. The observing step may include a quantitative observation for evaluating dispersion of the filler models 7. For example, the quantitative observation may include calculating a radial distribution function of the filler models a computer, and comparing it with respect to a predetermined threshold.

As a result of the step of observing, when it is judged that dispersion of the filler models 7 is not satisfactory, the configuration of the polymer models 3 are revised by changing the number of the modified basal particles 5, for example. Then the molecular dynamics calculation may be performed again in a similar fashion described above to find the better dispersion of filler models 7 among the polymer models 3. Finally, a developer may design an actual high polymer material based on the better configuration of polymer models 3 found in the simulation.

Figure 4:
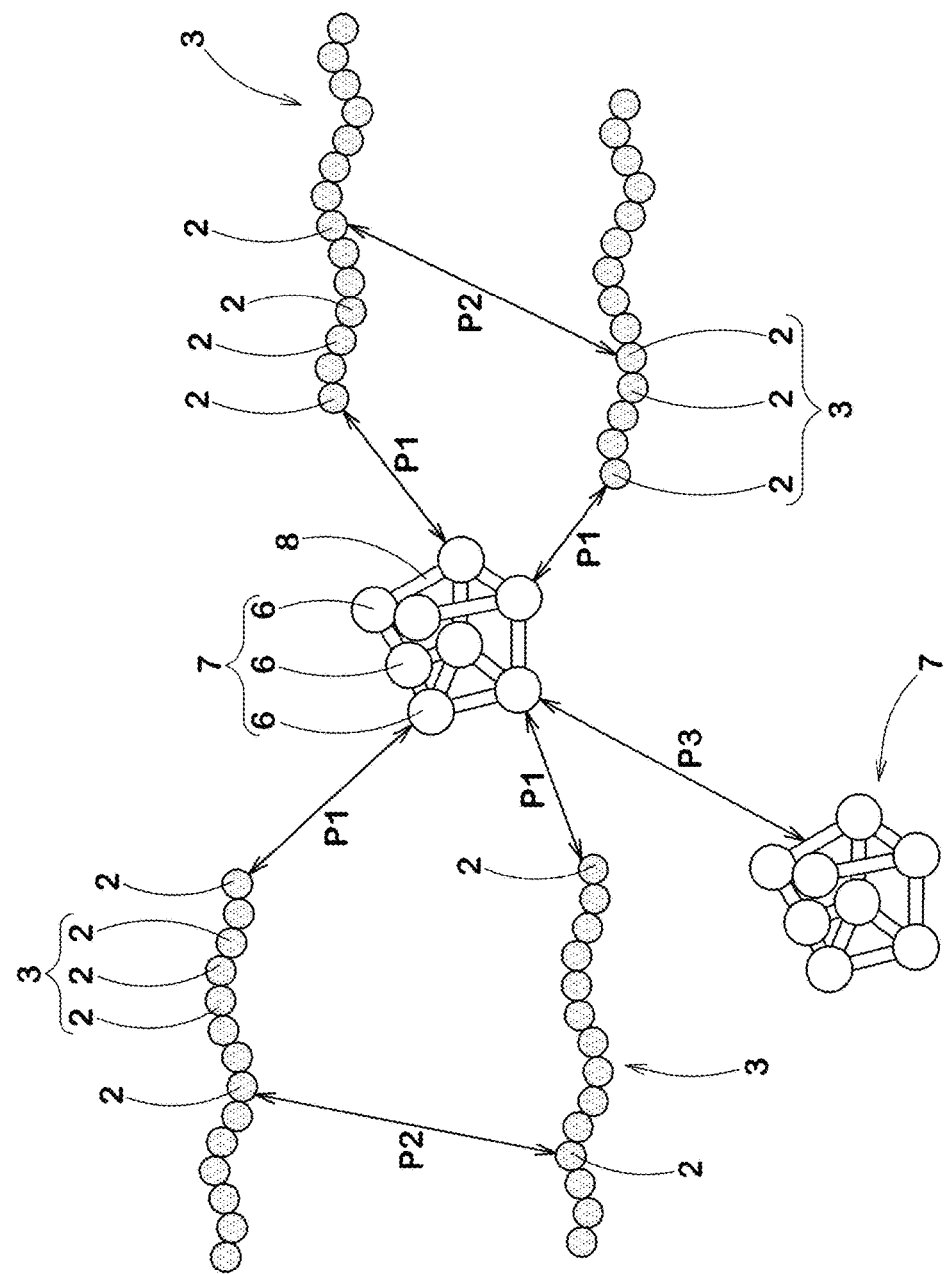
FIG. 4 is a diagram illustrating a polymer model without the modified basal particle.
Figure 5:
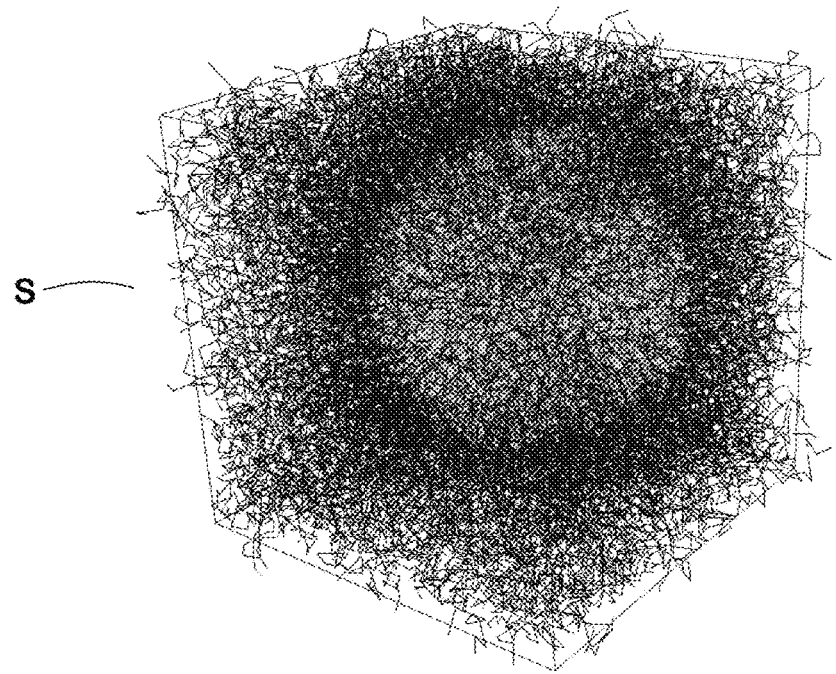
FIG. 5 is a perspective view of the simulation model using the polymer model without the modified basal particle in a state after performing the molecular dynamics calculation.

FIG. 4 illustrates visualized polymer models 3 without the modified basal particle 5. FIG. 5 illustrates a result of the visualized polymer models and filler models shown in FIG. 4 after performing the molecular dynamics calculation. As shown in FIG. 5, when the polymer models 3 without the modified basal particle 5 and the filler models 7 are used in the molecular dynamics calculation, it appears that the filler models 7 tend to condense like a sphere at a central region of the cell. Thus it might be difficult to obtain better dispersion of filler models 7.

In the embodiment described above, although the modified basal particle 5 is provided at one end of the polymer model 3, the modified basal particle 5 may be provided at both ends of the polymer model 3. In another aspect of the embodiment, the modified basal particle 5 may further be provided at a halfway of the polymer model 3. In another aspect of the embodiment, the affinity of the modified basal particle 5 to the particle 6 of the filler model 7 may be controlled by changing the parameter $a_{ij}$.

In another aspect of the embodiment, a linking condition may further be defined between the modified basal particle 5 of the polymer model and the particle 6 of the filler model 7. The linking condition is to link the particle 6 of the filler model 7 to the modified basal particle 5 of the polymer model when the modified basal particle 5 approaches the particle 6 of the filler model 7 within a predetermined distance in the molecular dynamics calculation. For example, a modified polymer includes one that bonds to a filler through chemical bond, and the other that bonds to a filler through physical adsorption. The embodiment of the present invention may help to evaluate which kind of modified polymer is advisable.

The present invention is more specifically described and explained by means of the following Examples and References. It is to be understood that the present invention is not limited to these Examples.

The invention claimed is:

1. A computerized simulation method for evaluating dispersion of fillers in a high polymer material, the method comprising:

defining a plurality of filler models available for use with the computerized simulation, the plurality of filler models comprising at least one particle;

defining a plurality of polymer models available for use with the computerized simulation, the plurality of polymer models comprising a plurality of particles each having a first potential with respect to the at least one particle of the filler models, and at least one modified basal particle having a second potential with respect to the at least one particle of the filler models, wherein the second potential differs from the first potential;

performing a molecular dynamics calculation of the plurality of filler models and the plurality of polymer models placed in a predetermined virtual space on the computer, wherein the plurality of filler models are dispersed due to interactions with the particles of the plurality of polymer models having the first potential or the second potential;

observing the dispersion of the filler models from data obtained in the molecular dynamics calculation by calculating a radial distribution function of the filler models;

revising a configuration of the polymer model by changing a number of the at least one modified basal particle when the radial distribution function of the filler models is below a predetermined threshold;

repeating the molecular dynamics calculation based on the revised configuration of the polymer model; and producing an improved simulation model including the filler models and the polymer models with the revised configuration, wherein the radial distribution function of the filler models of the improved simulation model is no less than the predetermined threshold, and the improved simulation model presenting a dispersion state of the filler models resembling a dispersion state of fillers in an actual polymer material that contains a modified agent.

2. The method according to claim 1, wherein the plurality of filler models comprise a plurality of particles.

3. The method according to claim 2, wherein the method further comprises linking the at least one particle of the plurality of filler models to the at least one modified basal particle of the plurality of polymer models, when the at least one modified basal particle of the plurality of polymer models approaches to the at least one particle of the plurality of filler models within a predetermined distance in the molecular dynamics calculation.

4. The method according to claim 2,
wherein each of the first potential and the second potential is defined so as to occur a repulsive force between two particles, and
the repulsive force based on the second potential is weaker than that of the first potential.

5. The method according to claim 1,
wherein the method further comprises linking the at least one particle of the plurality of filler models to the at least one modified basal particle of the plurality of polymer models, when the at least one modified basal particle of the plurality of polymer models approaches to the at least one particle of the plurality of filler models within a predetermined distance in the molecular dynamics calculation.

6. The method according to claim 5,
wherein each of the first potential and the second potential is defined so as to occur a repulsive force between two particles, and
the repulsive force based on the second potential is weaker than that of the first potential.

7. The method according to claim 1,
wherein each of the first potential and the second potential is defined so as to occur a repulsive force between two particles, and
the repulsive force based on the second potential is weaker than that of the first potential.

* * * * *